(12) United States Patent
Wei et al.

(10) Patent No.: US 10,626,387 B2
(45) Date of Patent: Apr. 21, 2020

(54) STAPHYLOCOCCUS LYSIN AND USE THEREOF

(71) Applicant: Phagelux, Inc., Grand Cayman (KY)

(72) Inventors: Hongping Wei, Wuhan (CN); Hang Yang, Wuhan (CN); Junping Yu, Wuhan (CN)

(73) Assignee: Phagelux, Inc., Grand Cayman (KY)

( * ) Notice: Subject to any disclaimer, the term of this patent is extended or adjusted under 35 U.S.C. 154(b) by 120 days.

(21) Appl. No.: 15/571,434

(22) PCT Filed: Apr. 12, 2016

(86) PCT No.: PCT/CN2016/079044
§ 371 (c)(1),
(2) Date: Nov. 2, 2017

(87) PCT Pub. No.: WO2016/184274
PCT Pub. Date: Nov. 24, 2016

(65) Prior Publication Data
US 2018/0291357 A1    Oct. 11, 2018

(30) Foreign Application Priority Data
May 18, 2015 (CN) .......................... 2015 1 0252947

(51) Int. Cl.
| | | |
|---|---|---|
| *C12N 9/36* | (2006.01) | |
| *C12N 15/70* | (2006.01) | |
| *C12N 15/62* | (2006.01) | |
| *C12N 9/48* | (2006.01) | |
| *C12Q 1/68* | (2018.01) | |
| *A61K 38/51* | (2006.01) | |
| *C12Q 1/66* | (2006.01) | |
| *C12Q 1/14* | (2006.01) | |
| *C12Q 1/527* | (2006.01) | |
| *C12N 9/88* | (2006.01) | |
| *C12N 9/80* | (2006.01) | |
| *C12N 1/06* | (2006.01) | |
| *C12Q 1/6806* | (2018.01) | |
| *C12Q 1/689* | (2018.01) | |
| *A61K 38/00* | (2006.01) | |

(52) U.S. Cl.
CPC ............ *C12N 9/2462* (2013.01); *A61K 38/51* (2013.01); *C12N 1/06* (2013.01); *C12N 9/485* (2013.01); *C12N 9/80* (2013.01); *C12N 9/88* (2013.01); *C12N 15/62* (2013.01); *C12N 15/70* (2013.01); *C12Q 1/14* (2013.01); *C12Q 1/527* (2013.01); *C12Q 1/66* (2013.01); *C12Q 1/68* (2013.01); *C12Q 1/6806* (2013.01); *C12Q 1/689* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 8,066,990 | B2 * | 11/2011 | Yoon ...................... | C12N 9/503 424/94.6 |
| 8,790,639 | B2 * | 7/2014 | Donovan ................ | A61K 38/48 424/94.3 |
| 9,057,059 | B2 * | 6/2015 | Grallert ................. | C12N 9/2462 |
| 9,872,893 | B2 * | 1/2018 | Nelson .................. | A61K 38/47 |
| 9,993,532 | B2 * | 6/2018 | Wei ........................ | A61K 38/51 |
| 10,022,430 | B2 * | 7/2018 | Grallert ................. | C12N 9/2462 |
| 10,053,681 | B2 * | 8/2018 | Fischetti ............... | C07K 14/005 |
| 10,301,607 | B2 * | 5/2019 | Scherzinger ........... | C12N 15/62 |
| 2010/0007321 | A1 * | 1/2010 | Ogram .................... | B64B 1/50 323/299 |
| 2010/0092968 | A1 * | 4/2010 | Beissinger ............ | C07K 14/005 435/6.13 |
| 2012/0258088 | A1 * | 10/2012 | Fischetti ............... | C07K 14/005 424/94.3 |
| 2013/0004476 | A1 * | 1/2013 | Grallert ................. | C12N 9/2462 424/94.3 |
| 2013/0259849 | A1 * | 10/2013 | Donovan ................ | A61K 38/48 424/94.3 |
| 2013/0288926 | A1 * | 10/2013 | Scherzinger ............ | C12Q 1/18 506/17 |
| 2014/0072549 | A1 * | 3/2014 | Fischetti ............... | A61K 38/162 424/94.61 |

(Continued)

FOREIGN PATENT DOCUMENTS

| | | |
|---|---|---|
| CN | 102676490 A | 9/2012 |
| CN | 103122347 A | 5/2013 |

(Continued)

OTHER PUBLICATIONS

Dong et al, Microbial Biotechnology, 2015, 8/2:210-220 (Year: 2015).*

(Continued)

*Primary Examiner* — Nita M. Minnifield
(74) *Attorney, Agent, or Firm* — Viksnins Harris Padys Malen LLP (57) ABSTRACT

The present invention discloses a lysin that is capable of killing *Staphylococcus* and the use thereof, belonging to the field of biological agents. The present invention discloses the amino acid sequence and the encoding gene sequence of the lysin. This lysin keeps active in a wide range of pH. It has lytic activity against *Staphylococcus* in pH 4-11. The recombinant protease constructed by the encoding gene can be solubly expressed in *E. coli* strain BL21 (DE3). The lysin can be used to effectively kill multiple species *Staphylococcus* in vitro, including methicillin sensitive *Staphylococcus aureus* (MSSA) and methicillin resistant *Staphylococcus aureus* (MRSA) isolated in clinics. This lysin can be used as an antibiotic for the treatment of staphylococcal infections in vivo. This lysin is also able to rapidly lyse staphylococcal cell wall; as a result, intracellular substances such as ATP and DNA are released. Those released substances can be used to detect the type of *Staphylococcus*.

9 Claims, 7 Drawing Sheets

Specification includes a Sequence Listing.

(56) References Cited

U.S. PATENT DOCUMENTS

| | | | | |
|---|---|---|---|---|
| 2014/0302004 A1* | 10/2014 | Donovan | ............... | C12N 9/52 424/94.63 |
| 2015/0238577 A1* | 8/2015 | Grallert | ............... | C12N 9/2462 424/94.3 |
| 2016/0038572 A1* | 2/2016 | Nelson | ............... | A61K 38/47 424/94.61 |
| 2017/0127683 A1* | 5/2017 | Schuch | ............... | C12N 9/503 |
| 2018/0104316 A1* | 4/2018 | Wei | ............... | A61K 38/51 |
| 2018/0147264 A1* | 5/2018 | Nelson | ............... | A61K 38/47 |
| 2018/0273549 A1* | 9/2018 | Sutton | ............... | C07D 501/22 |
| 2018/0291357 A1* | 10/2018 | Wei | ............... | A61K 38/51 |
| 2019/0055533 A1* | 2/2019 | Fischetti | ............... | C07K 14/005 |
| 2019/0169623 A1* | 6/2019 | Starzl | ............... | C12N 15/78 |
| 2019/0290672 A1* | 9/2019 | Wittekind | ............... | A61P 31/04 |

FOREIGN PATENT DOCUMENTS

| | | | | |
|---|---|---|---|---|
| CN | 104805066 A | 7/2015 | | |
| EP | 3299459 A1 * | 3/2018 | ............ | A61K 38/51 |
| WO | 2004020635 A1 | 3/2004 | | |
| WO | WO-2010041970 A2 * | 4/2010 | ............ | C12N 9/503 |
| WO | WO-2011076432 A1 * | 6/2011 | ............ | C12N 9/2462 |
| WO | WO-2014039436 A1 * | 3/2014 | ..... | C12Y 302/01017 |

OTHER PUBLICATIONS

Qiao et al, Enzyme and Microbial Technology, 2016, 95:64-99. Available online: Sep. 20, 2016 (Year: 2016).*
Yang et al, EMBO Journal, 2018, 37:e98045. 15 pages. Published online: Jul. 23, 2018 (Year: 2018).*
Zhou et al, Research in Veterinary Science, 2017, 111:113-119 (Year: 2017).*
Singh et al, Antimicrobial Agents and Chemotherapy. Aug. 2014, 58/8:4621-4629. Published ahead of print: Jun. 2, 2014 (Year: 2014).*
Liu et al, Nanoscale, 2015. 7:15245-15250 (Year: 2015).*
Yang et al, Antimicrobial Agents and Chemotherapy, Jan. 2014, 58/1:536-542. Published ahead of print: Nov. 4, 2013 (Year: 2014).*
Mao et al, FEMS Microbiology Letters. 2013, 342/1:30-36. (Year: 2013).*
Fischetti, Current Topics Microbiology and Immunology, 2017, 409:529-540. Published online: Jan. 5, 2016 (Year: 2017).*
International Preliminary Report on Patentability in PCT/CN2016/079044, dated Nov. 21, 2017, 6 pages.
PCT International Search Report in PCT/CN2016/079044, dated Jul. 1, 2016, 3 pgs.

* cited by examiner

STAPHYLOCOCCUS LYSIN AND USE THEREOF

CROSS REFERENCE TO RELATED APPLICATIONS

This is a National Phase entry of International Application No. PCT/CN2016/079044, filed, Apr. 12, 2016, which claims priority to Chinese Patent Application No. CN201510252947.6, filed May 18, 2015, the disclosures of which are incorporated herein by reference in their entireties.

REFERENCE TO SEQUENCE LISTING

The material contained in the text file identified as "LAPCT160316US-WO2016184274 A1-Sequence List-ClyO" (created Mar. 6, 2018, 6.4 kilobytes) is hereby incorporated by reference.

TECHNICAL FIELD

The present invention belongs to the field of biologic agents, in particular, relates to a lysin that is able to kill Staphylococci, especially *Staphylococcus aureus*; and use thereof on killing and detection of Staphylococci.

BACKGROUND

According to the differences in biochemical reaction and pigment production, *Staphylococcus* can be divided into three species, *Staphylococcus aureus*, *Staphylococcus epidermidis* and *Staphylococcus saprophyticus*. Among them, *Staphylococcus aureus* is mostly pathogenic, *Staphylococcus epidermidis* occasionally pathogenic and *Staphylococcus saprophyticus* generally is non-pathogenic. *Staphylococcus aureus* is a common gram-positive coccus that causes many serious infections in humans and animals. It is also one of the common pathogens in hospital infections. *Staphylococcus* easily becomes resistant to antibiotics, including various common antibiotics and novel antimicrobial agents. The emergence and widespread of methicillin resistant *Staphylococcus aureus* (MRSA) has brought unprecedented challenges to clinical treatment. In order to deal with the problem of resistance to antibiotics in *Staphylococcus*, it is necessary to extract staphylococcal genome DNA for PCR to detect whether the clinical strains are MRSA and so on. However, owing to the tough cell wall of *Staphylococcus*, the normal egg white lysozyme has no obvious lytic effect on it, while lysostaphin that has good lytic activity against staphylococcal cell wall is too expensive to be widely applied.

Phage lysin is a kind of cell wall hydrolase expressed in late stage after host bacteria being infected with dsDNA phage. The size of lysins is normally in the range of 25 kD-40 kD, they are usually composed of two independent functional domains in the structure, the N-terminal catalytic domain, and a C-terminal cell wall binding domain (CBD) that determines cell binding sites. The two domains are linked by a small fragment. Sequence analysis shows that the catalytic domain of the same type lysin is highly conserved while the cell binding domain is variable, which provides the possibility for constructing new chimeric lysins. Lysins are highly specific and can only specifically identify and kill specific species of bacteria. Moreover, the action site of lysins is very conservative and coevolution of specificity of phage and bacterial makes it difficult for host bacteria to become resistant to them. These characteristics of lysins provide theoretical feasibility for the control and treatment of drug-resistant bacteria in clinical practice. So far, there are some natural lysins and chimeric lysins that have effect on *Staphylococcus aureus*. These enzymes have been reported to be able to kill *Staphylococcus aureus* well in vivo and in vitro. However, most of these lysins are difficult to be solubly expressed, or the activity is not high or they cannot adapt to protein-rich environment (such as milk, etc.), and the pH range to keep them to be active is narrow, generally in pH 5-8. It is very importantly significant to look for lysins which are solubly expressed in high level and have high activity for development of new anti-staphylococcal medicine and control of staphylococcal infections in vitro, and for detection of *Staphylococcus* by lysing its cell wall.

DISCLOSURE OF INVENTION

The technical problem to be solved in the present invention is to provide a *Staphylococcus* lysin which is solubly expressed and has high activity and use thereof. This lysin can kill Staphylococci, especially *Staphylococcus aureus* in vitro and in vivo. For the convenience of narration, we name this new lysin as ClyO, and its encoding gene as ClyO.

The nucleic acid sequence of the staphylococcal lysin of the encoding gene ClyO provided in the present invention is shown in SEQ.ID.NO.1 in the sequence list.

The protein sequence of the staphylococcal lysin ClyO provided in the present invention is shown in SEQ.ID.NO.2 in the sequence list.

The present invention also discloses a method to solubly express and purify ClyO protein, which comprises the following steps: the ClyO gene is cloned and then ligated with the expression vector pBAD24, then the expression plasmid was transformed into *E. coli* BL21 (DE3) to express. The expressed protein is purified by ion exchange followed by treatment with dialytic phosphate buffer (PBS).

The present invention confirms that the lysin ClyO has high activity and broad spectrum of killing *Staphylococcus*. The present invention discloses the use of ClyO in killing *Staphylococcus epidermidis*, *Staphylococcus saprophyticus*, *Staphylococcus equorum*, *Staphylococcus capitis*, *Staphylococcus albus*, *Staphylococcus xylosus*, *Staphylococcus sciuri*, *Staphylococcus haemolyticus*, *Staphylococcus chromogene*, and *Staphylococcus aureus* in vitro. The *Staphylococcus aureus* mentioned above comprises clinically isolated methicillin sensitive *Staphylococcus aureus* (MSSA) and methicillin resistant *Staphylococcus aureus* (MRSA). The invention preliminarily tested the protective effect of ClyO on the experimental animal mice model infected with *Staphylococcus aureus*, and tested the cytotoxicity, which initially confirmed the potential of the medicine preparation for the development of anti-staphylococcal infections.

The invention further discloses the use of the lysin ClyO in the detection and identification of *Staphylococcus*. After the interaction between ClyO and bacteria to be tested, cellular substances such as adenine phosphate (ATP) or DNA will be released from bacteria which can be used to detect and identify the *Staphylococcus*.

The invention further discloses the characteristics of rapid lysis of *Staphylococcus* cell walls and releasing of intracellular ATP by using ClyO, and a method for rapid identification of *Staphylococcus* by detecting released ATP using luciferase. The method comprises the following steps: mixing ClyO with the bacteria to be tested, adding luciferase and its substrate for incubating at 37° C., at the same time using microplate reader to detect the fluorescence intensity change of the mixture, and preparing a negative control via using bacteria mixture in the absence of ClyO.

The invention also discloses the characteristics of rapid lysis of Staphylococcus cell walls and releasing of intracellular DNA by using ClyO, and a method for detection and identification of Staphylococcus by PCR method using released DNA in the lysis buffer as a template. As an example, detection results for MRSA identification and typing are provided. The method comprises the following steps: mixing ClyO with the bacteria to be tested and incubating at 37° C. for 10-15 min, centrifuging the mixture at 10,000 g for 1 min; pipetting the supernatant as a template, adding two pairs of primers confirmed by MRSA (for femB and mecA respectively) for PCR to detect whether a strain is MRSA or not. For the confirmed MRSA strains, using 4 pairs of Staphylococcal Cassette Chromosome Mec (SCCmec) primers for PCR to confirm their SCCmec strain type.

The lysin of the present invention has the following outstanding effects and advantages:

ClyO can kill various Staphylococcus aureus in vivo and in vitro, including a variety of clinical isolates of Staphylococcus aureus and MRSA strains. ClyO has low cytotoxicity and has the potential to be used as an anti-infective medicine in vivo. ClyO can be solubly expressed in Escherichia coli and is suitable for fermentation production. ClyO has a high enzyme activity and keeps high activity in the range of pH 4-11.

DETAILED DESCRIPTION OF THE INVENTION

The present invention is further explained by the following examples, but the present invention is not to be limited by this.

The present inventors designed and artificially synthesised the gene sequence that is able to express a kind of Staphylococcus lysin ClyO, and obtained this enzyme by in vitro recombination and expression in E. coli, through analysis of the amino acid sequences of the catalytic domain and the cell structure domain of Staphylococcus phage lysin.

The following methods used in examples were standard experimental methods without special description. All primers used in experiments were provided by Invitrogen (Shanghai). DNA sequencing was performed by Invitrogen (Shanghai). The standard S. aureus CCTCC AB91118 strain was purchased from Culture Collection Center of University of Wuhan, S. epidermidis ATCC 12228 strain and reference strain were purchased from Guangdong Culture Collection Center. Other strains were isolated in clinics from several hospitals in Wuhan, and were identified by Biolog Automatic Analyzer for Microbes. The drug resistance of clinical bacterial strains was verified by methicillin paper disk dilution method. The clinical isolates of S. aureus were streaked on the Baird-Parker agar (purchased from Guangdong Huankai Microbial Sci. & Tech. Co., Ltd.); then single colony was picked, and then cultured overnight in TSB medium for testing use.

EXAMPLE 1

Construction of the Lysin being Able to Kill Staphylococcus

1) DNA sequences of ClyO gene expressing lysin ClyO was totally synthesised by Sangon Biotech (Shanghai) Co., Ltd. The synthesised sequences was inserted into plasmid pUC57. The ClyO gene was used as a template, and restriction enzyme sites NcoI and XhoI were introduced at two terminals of the target gene. Primers were designed as below:

```
Forward primer:
                                     (SEQ.ID.NO. 3)
5-TTAACCATGGGCATGGCACTGCCTAAAACG-3
    NcoI Reverse primer:
                                     (SEQ.ID.NO. 4)
5-ATATCTCGAGTTTAAATGTACCCCAAGC-3
    XhoI
```

2 µl of gene was used as a template, then 1 µg of each primer was added for PCR amplification, and the programme of PCR amplification was described as below:

1) 94° C., 5 min;
2) 94° C., 30 sec, 62° C., 45 sec, 72° C., 45 sec, 30 cycles;
3) 72° C., 10 min.

Figure 1:
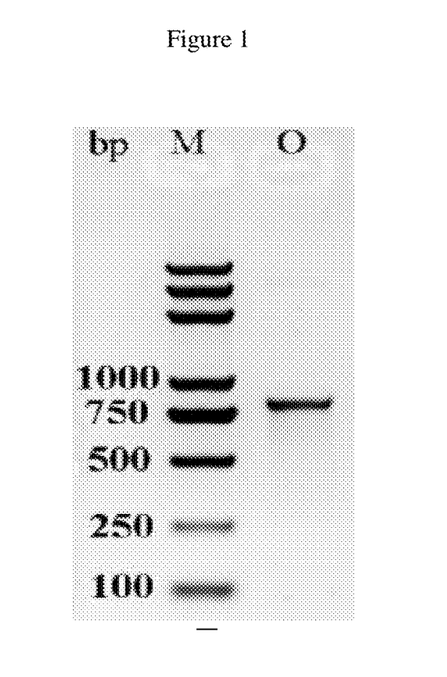
FIG. 1 is the results of PCR amplification of ClyO gene. In the figure, the lane M represents standard DNA marker, the size of the bands is shown on the left. The lane O is the band of amplified ClyO.

PCR products were electrophoresed and recovered, electrophoretic pattern was shown in FIG. 1. The size of ClyO gene was 777 bp, which was consistent with the size of designed lysin gene.

2) The ClyO gene was ligated with expression plasmid pBAD24 to obtain recombinant plasmid pB-ClyO, and then this recombinant plasmid was transformed into *E. coli* strain BL21(DE3).

3) Expression and Purification of ClyO

Expression strain BL21(DE3)/pB-ClyO was induced by using 0.2% L-arabinose under low temperature. Bacteria were collected, and then broke by sonication. The supernatant was precipitated out by 33% ammonium sulfate, and the precipitates were dissolved in PBS, then dialysed against PBS overnight. The dialysate has obvious anti-bacterial activity.

The crude extract solution after dialysis or the supernatant after sonication was passed through a HiTrap Q Sepharose FF column (GE Healthcare), and the effluent was collected. The effluent was then passed through a HiTrap SP Sepharose FF column, then samples were gradient-eluted by 1M NaCl, and elution peaks were collected in sections. The fractions with activity were combined, and then dialysed against PBS overnight; the resulting sample was the purified enzyme.

EXAMPLE 2

Verification of the Effect of ClyO on Killing Standard *S. aureus* Strain CCTCC AB91118

Figure 2:
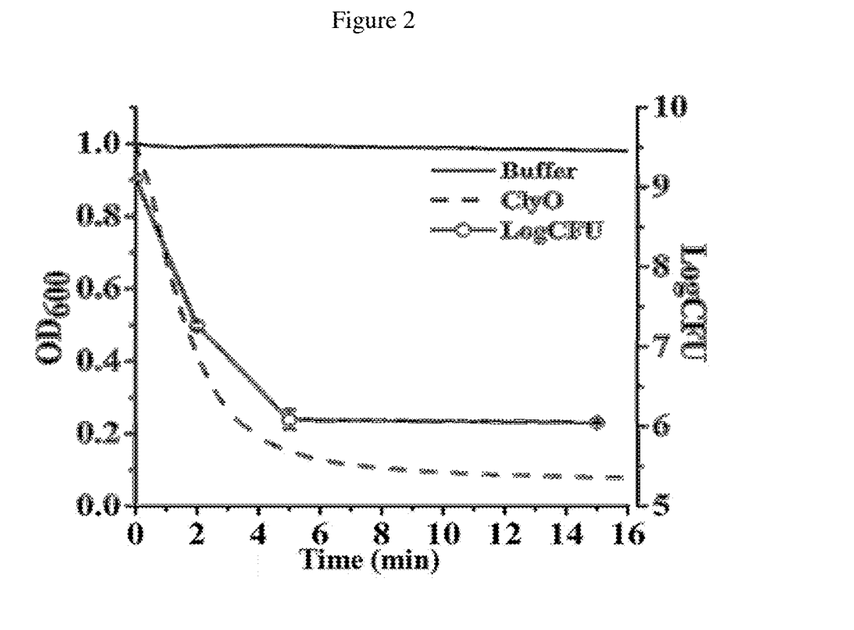
FIG. 2 is the results of ClyO killing Staphylococcus aureus standard strain CCTCC AB91118. The dotted line shows the change trend of $OD_{600}$ absorbance over time after Staphylococcus aureus being mixed with ClyO. The solid line shows the change trend of $OD_{600}$ absorbance over time after Staphylococcus aureus being mixed with buffer. The hollow circle shows the change trend of Log CFU over time after Staphylococcus aureus being mixed with buffer.

*S. aureus* was cultured overnight and collected by centrifugation, and then washed with PBS once, re-suspended in PBS. A quantity of ClyO was mixed with the above bacteria, at the same time, the change of absorbance at 600 nm was monitored by a microplate reader. The mixtures of buffer and *S. aureus* bacteria were used as a negative control. The final lysis curve was obtained as shown in FIG. 2. At the same time, the number of viable bacteria treated at different time was counted on plates after serial dilution. This result showed that CCTCC AB91118 strain was rapidly lysed by ClyO, as a result, turbidity of bacteria suspension dropped, which was shown as the absorbance at 600 nm was rapidly declined.

EXAMPLE 3

Figure 3:
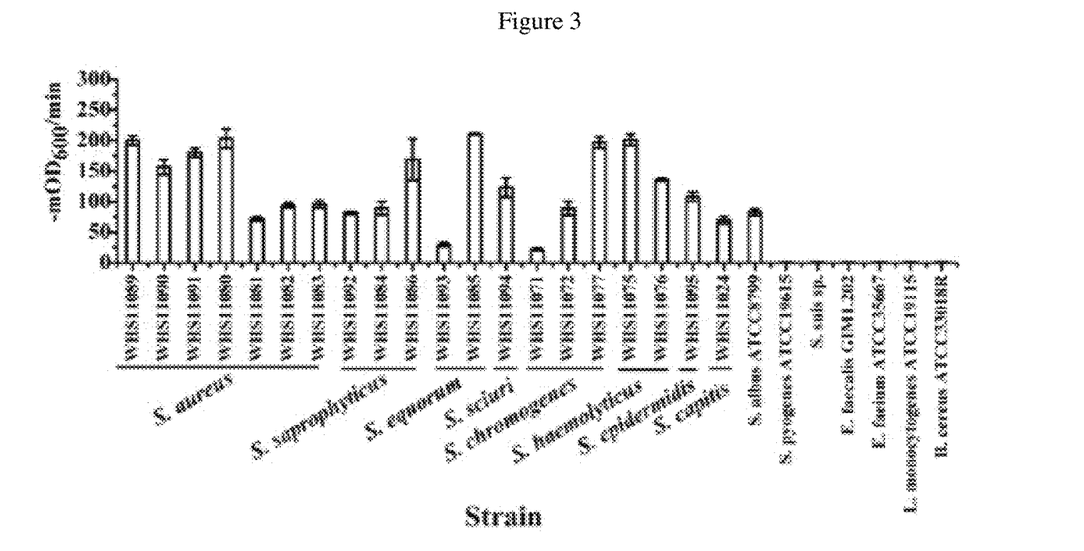
FIG. 3 is the results of specificity of ClyO killing various Staphylococcus strains and against different variety of bacterial strains in vitro. The vertical coordinates show the decrease rate of $OD_{600}$ absorbance after incubating the mixtures of various bacterial strain and ClyO at 37° C. for 30 min.

Verification of the Specificity of ClyO Against Various Staphylococci In Vitro and Other Different Type of Bacteria To verify the lytic spectrum of ClyO, several non-*Staphylococcus* strains stored in the lab of the inventors and clinical isolates including *S. aureus*, *S. epidermidis*, *S. saprophyticus*, *S. equorum*, *S. sciuri*, *S. haemolyticus*, *S. chromogenes* and some other strains were selected and tested. Firstly, every testing strain was cultured overnight, and then collected by centrifugation, and washed with PBS once, then re-suspended in PBS. A quantity of ClyO was mixed with the above bacteria; at the same time, the change of absorbance at 600 nm was monitored for 30 min by a microplate reader. The declining rate of $OD_{600}$ was used to indicate the lytic effect of ClyO against different strains. The mixtures of buffer and bacteria suspensions were used as a negative control. The killing effect obtained from the experiment was shown in FIG. 3. This result showed that ClyO was able to rapidly kill various clinically isolated Staphylococci strains, but showed no effect on other types of bacteria.

EXAMPLE 4

The Effect of ClyO on Eliminating of Various Staphylococcal Strains in Milk

Figure 4:
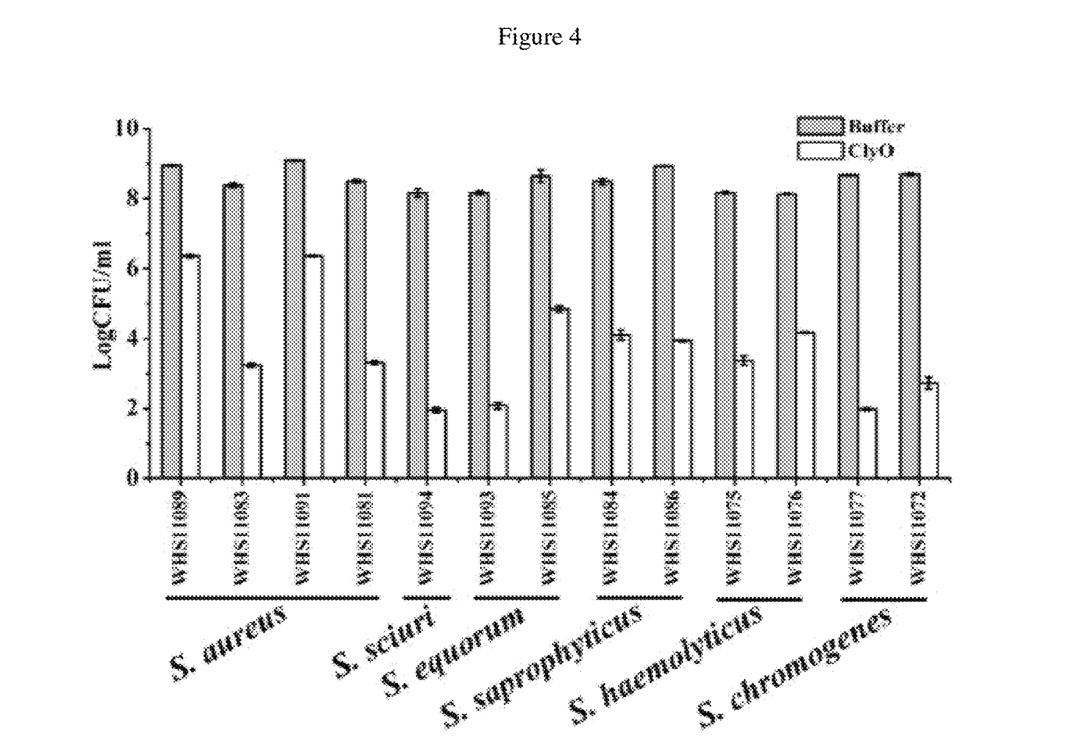
FIG. 4 is the results of ClyO killing MRSA in milk. The vertical coordinates show the decrease of the log value after incubating the mixtures of various bacterial strains and ClyO at 37° C. for 60 min.

Various types of MRSA isolated clinically were cultured overnight, then collected by centrifugation, followed by PBS wash once, and then re-suspended in sterile pasteurized milk. A quantity of ClyO was mixed with the above bacterial suspension and mixed well respectively, the reaction suspension was placed at 37° C. for 60 minutes, and then the number of viable bacteria was calculated by number counting on plates by serial dilution. The killing effect obtained from the experiment was shown in FIG. 4. This result showed that ClyO was able to rapidly kill various Staphylococci in milk.

EXAMPLE 5

Figure 5:
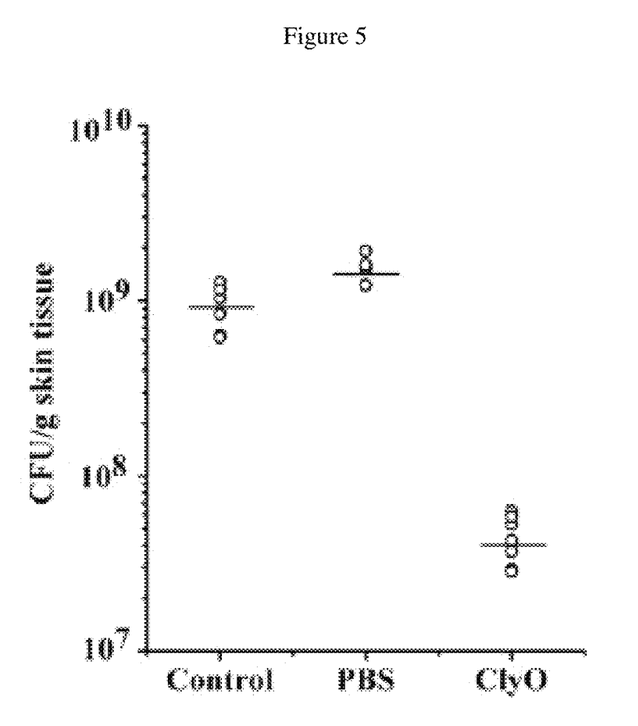
FIG. 5 is the results of ClyO eliminating MRSA on the infected skin of scalded mice. For each group (20 mice), high concentration of MRSA was inoculated on the scalded skin, then the mice were treated with PBS and 100 mg ClyO after 24 h. After treatment for 24 h, skins were cut off and the MRSA numbers were calculated in each tissue sample by the method of serial dilution followed by colony-counting on the plate. No treatment was done in the control group after inoculation of the bacteria.

The Effect of ClyO on Eliminating Infection Caused by MRSA on Scalded Mice Skin Tissue Female BALB/c mice (6 weeks old, weighing 20-22 g) were used in the experiment. Backs of experimental mice (60 mice) were scalded by exposure of the naked skin in water at 80° C. for 10 s. Then $1 \times 10^7$ CFU MRSA was inoculated on scalded wounds. After 24 h, mice were divided into three groups with 20 mice in each group. The experimental groups were treated with 100 mg ClyO or sterile PBS respectively, while the control group was left without treatment. The viable bacteria load per unit of the scald skin tissue was calculated after 24 h. The results were shown in FIG. 5. This result showed that ClyO was able to effectively reduce the viable MRSA load on scalded skin tissues.

EXAMPLE 6

Verification of the Effect of ClyO on Killing *Staphylococcus* In Vivo

Figure 6:
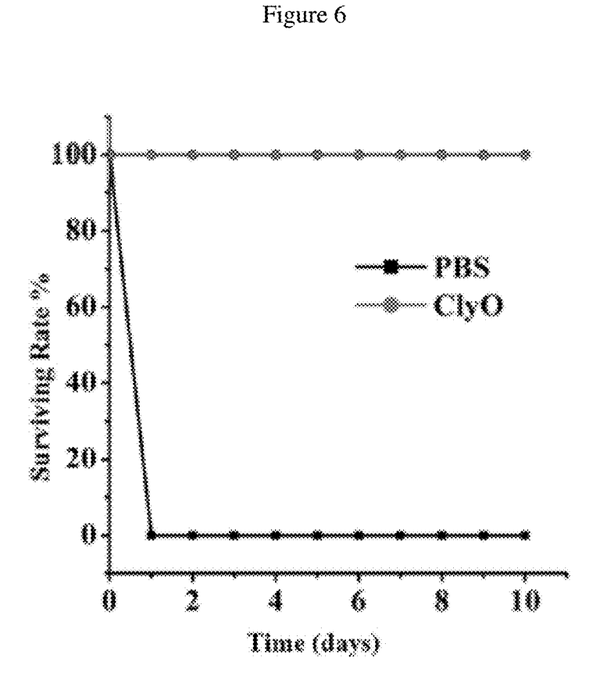
FIG. 6 is the results of ClyO killing Staphylococcus aureus in vivo. For each group (20 mice), lethal dose of Staphylococcus aureus was injected respectively. For the experimental group 1 mg ClyO was injected intraperitoneally after 3 h. For the control group, same volume of PBS was injected intraperitoneally after 3 h. The survival rate for each group was observed every day.

Female BALB/c mice (6 weeks old, weighing 20-22 g) were used in the experiment. 40 experimental mice were injected intraperitoneally with 6×10⁷ CFU *S. aureus* stain WHS11081 isolated clinically. After three hours, mice were divided into 2 groups, and each group had 20 mice. Mice in the experimental group were injected intraperitoneally with 1000 µg of ClyO, mice in the control group were injected with PBS. The survival rates were observed every day. The results were shown in FIG. 6. The results showed that ClyO was able to kill MRSA in vivo effectively in mice, thus the survival rates of mice were increased.

EXAMPLE 7

Test of the Cytotoxicity of ClyO

Figure 7:
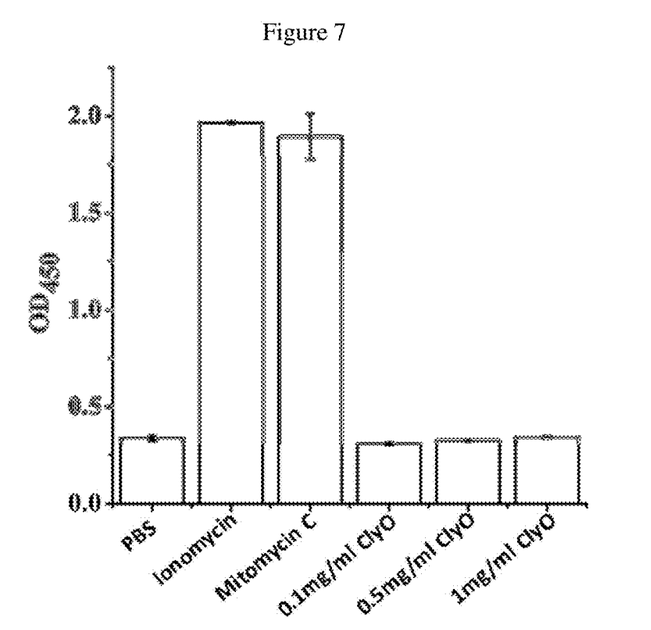
FIG. 7 is the tested cytotoxicity result of ClyO. No significant cytotoxicity was observed for ClyO at a concentration of 0.1 mg/ml, 0.5 mg/ml, and 1 mg/ml on Caco-2 cells respectively. Ionomycin and mitomycin C were used as positive controls which were known to be toxic to cells.

Caco-2 cells were inoculated into 96 well plates at a concentration of 5×10³ cells per well. After being cultured for 24 hours, A quantity of concentration of ClyO (0.1-1 mg/ml), Ionomycin (15 mg/ml) and mitomycin (15 mg/ml) were added into wells. Cells were further cultured for 24 hours. A staining regent WST-8 was added into wells after the incubation was finished, and then the absorbance at 450 nm was measured after standing still. The results were shown in FIG. 7. This result showed that there was no cytotoxicity caused by ClyO even at high concentration, but Ionomycin and mitomycin as positive controls showed higher cytotoxicity.

EXAMPLE 8

Use of ClyO for Rapid Detection of *Staphylococcus* Based on Release of ATP

Figure 8:
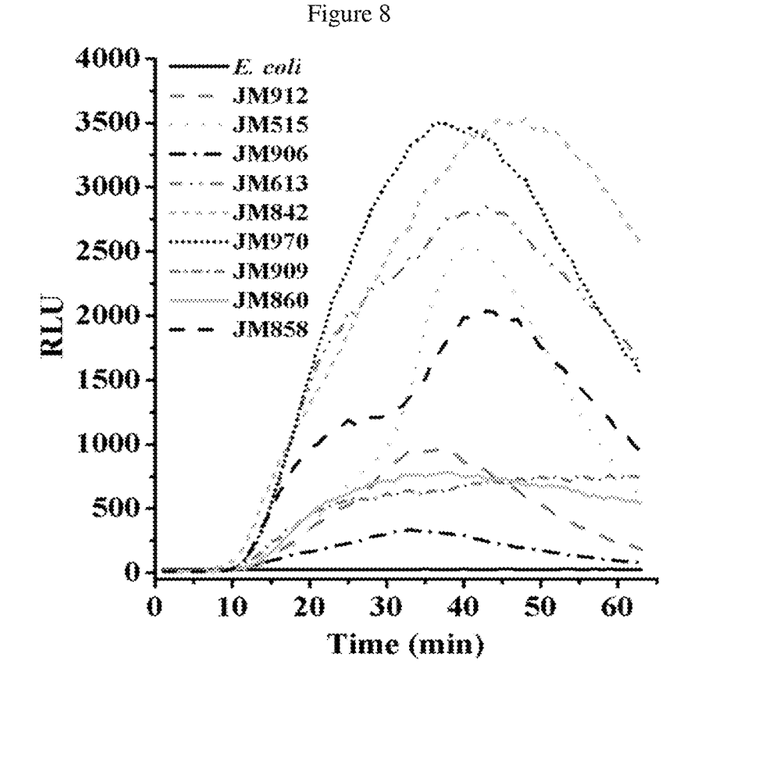
FIG. 8 is the results of rapid detection of Staphylococcus aureus type based on ATP release using ClyO. The black solid line represents the blank control. The rising curve represents different Staphylococcus aureus strains.

*S. aureus* and *E. coli* were cultured overnight and collected by centrifugation, and then washed with PBS once, and then re-suspended in PBS. A quantity of ClyO was mixed with the above bacterial suspension, at the same time 0.25 µM luciferase and 5 µM fluorescein substrate containing 12.5 µM coenzyme A were added. The reaction mixture was placed at 37° C. after being mixed well, and then the fluorescence intensity of the mixture was detected by a microplate reader. The results were shown in FIG. 8. This result showed that tested staphylococcal cultures were fluoresced at different degree. Obviously, it was caused by the lysis of the cell wall of *Staphylococcus* using ClyO which leaded to the release of ATP from cells. Luciferase could use the released ATP to catalyze the luminescence of the substrate. However, in *E. coli* solution being used as the blank control, no luminescence light was detected, because no ATP was released from *E. coli* that was not able to be lysed by ClyO.

EXAMPLE 9

PCR Identification of the Effect of ClyO on MRSA Strain

Figure 9:
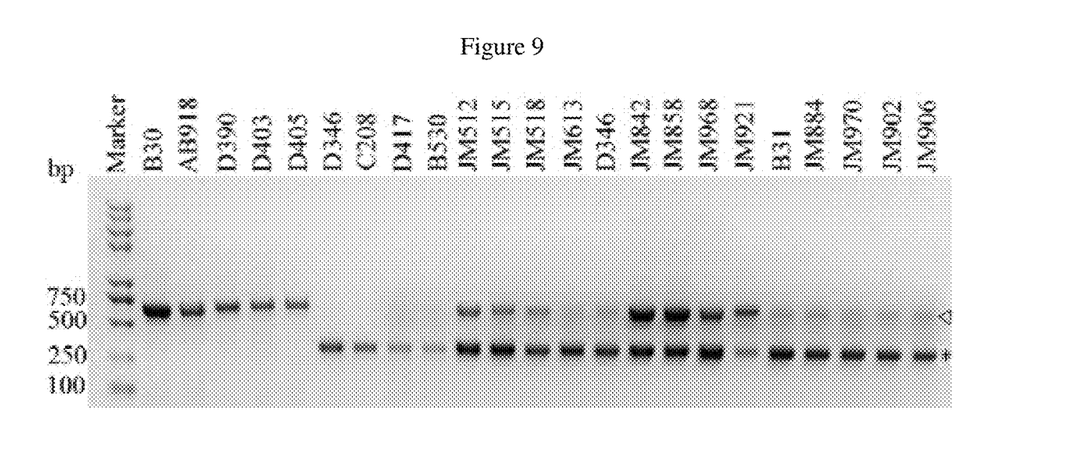
FIG. 9 is the PCR detection results of identifying MRSA using ClyO. The position represented by triangle is femB gene, the position represented by the star is mecA gene. MRSA strains contains both femB and mecA genes, while MSSA strains contain only femB. Other Staphylococcus aureus strains only contain mecA.

Various *S. aureus* isolated in clinics were cultured overnight and collected by centrifugation, and then washed with PBS once, and then re-suspended in PBS. A quantity of ClyO was mixed with the above bacterial suspension, then lysed at 37° C. for 10-15 min. Lytic solution was then centrifuged at 10,000 g for 1 min. 1 µL of supernatant was used as template, and 1 µg primers was added respectively for PCR amplification. Primers used to amplify femB gene were: FemB-F (5'-TTACAGAGTTAACTGTTACC-3') (SEQ.ID.NO.5) and FemB-R (5'-ATACAAATCCAG-CACGCTCT-3') (SEQ.ID.NO.6); primers used to amplify mecA gene were MecA-F (5'-GTAGAAATGACT-GAACGTCCGATAA-3') (SEQ.ID.NO.7) and MecA-R (5'-CCAATTCCACATTGTTTCGGTCTAA-3') (SEQ.ID. NO.8). The PCR amplification program was as follows: 1) 94□, 5 min; 2) 94° C., 30 sec, 50° C., 45 sec, 72° C., 60 sec, 30 cycles; 3) 72° C., 10 min. PCR products were analysed by electrophoresis, and the electrophoretic pattern was shown in FIG. 9. The size of femB gene is 651 bp, and the size of mecA gene is 310 bp. MRSA strains contain both genes, and MSSA strains contain only femB. Other types of *S. aureus* strains only contain mecA. This result showed that it was convenient to identify MRSA strain by PCR by using the lytic supernatants of *S. aureus* after ClyO treatment.

EXAMPLE 10

Verification of PCR Identification of MRSA Strain Typing by ClyO

Figure 10:
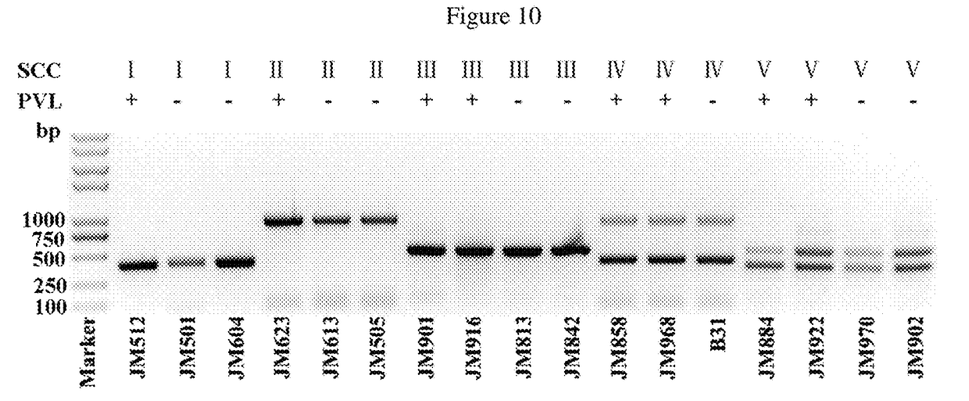
FIG. 10 is the PCR detection results of MRSA strain typing using ClyO. The size of the band obtained by PCR SCCmec type I strain is 415 bp. the size of the band obtained by SCCmec type II strain PCR is 937 bp. The size of the band obtained by SCCmec type III strain PCR is 518 bp. The size of the two bands obtained by SCCmec type IV strains PCR are 415 bp and 937 bp respectively. The size of the two bands obtained by SCCmec type V strains PCR are 518 bp and 359 bp respectively.

MRSA isolated in clinics were cultured overnight and collected by centrifugation, and then washed with PBS once, and then re-suspended in PBS. A certain amount of ClyO was mixed with the above bacterial suspension, and lysed at 37° C. for 10-15 min, and then centrifuged at 10,000 g for 1 min. 1 µL of supernatant was used as a template, and 1 µg of primers required for typing were added for PCR amplification. The PCR amplification program was follows: 1) 94° C., 5 min; 2) 94° C., 30 sec, 50° C., 30 sec, 72° C., 30 sec, 30 Cycles; 3) 72° C., 10 min. PCR products were analyzed by electrophoresis, and the electrophoretic pattern was shown in FIG. 10. The results showed that the supernatant after ClyO lysis could be conveniently used as the template for PCR analysis of MRSA typing. Different types of MRSA could be well characterized. The 4 pairs of primers used for MRSA typing and their characterizations were as follows:

| Primer | Sequence (5'-3') | Size (bp) | Target gene | SCCmec type | | | | |
|---|---|---|---|---|---|---|---|---|
| | | | | I | II | III | IV | V |
| β | ATTGCCTTGATAATA GCCYTCT (SEQ ID NO: 9) | 937 | ccrA2-B | | X | | X | |
| α3 | TAAAGGCATCAATG CACAAACACT (SEQ ID NO: 10) | | | | | | | |
| ccrCF | CGTCTATTACAAGAT GTTAAGGATAAT (SEQ ID NO: 11) | 518 | ccrC | | | X | | X |

| Primer | Sequence (5'-3') | Size (bp) | Target gene | SCCmec type | | | | |
|---|---|---|---|---|---|---|---|---|
| | | | | I | II | III | IV | V |
| ccrCR | CCTTTATAGACTGGA TTATTCAAAATAT (SEQ ID NO: 12) | | | | | | | |
| 1272F1 | GCCACTCATAACAT ATGGAA (SEQ ID NO: 13) | 415 | IS1272 | | X | | X | |
| 1272R1 | CATCCGAGTGAAAC CCAAA (SEQ ID NO: 14) | | | | | | | |
| 5RmecA | TATACCAAACCCGA CAACTAC (SEQ ID NO: 15) | 359 | mecA-IS431 | | | | X | |
| 5R413 | CGGCTACAGTGATA ACATCC (SEQ ID NO: 16) | | | | | | | |

EXAMPLE 11

Figure 11:
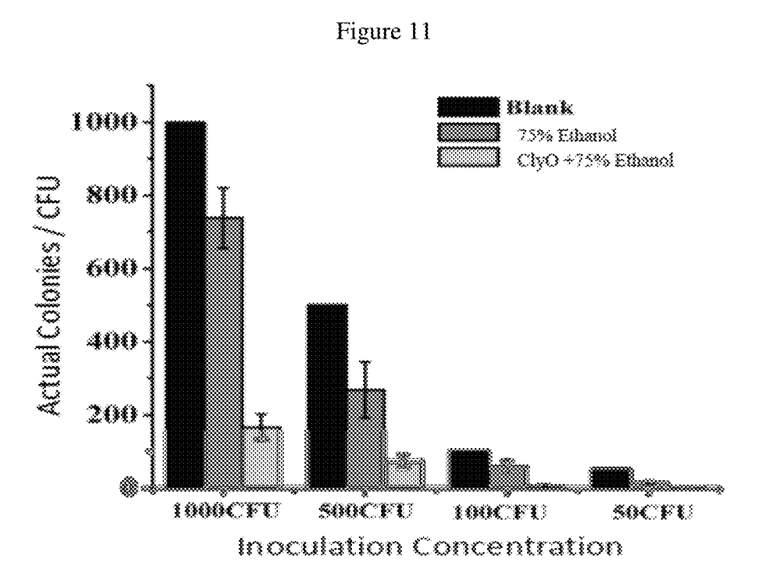
FIG. 11 is the results of reduction of the number of Staphylococcus aureus after mimic skin disinfection using ClyO. The Staphylococcus aureus can be completely eliminated by ClyO when the inoculated amount of bacteria is less than 100 CFU.

The Effect of ClyO on Reducing the Number of *Staphylococcus* after Simulated Skin Disinfection Different concentrations of *S. epidermidis* were spread on naked skin of mice, and was dried in the air naturally for test. During test, the experimental group was firstly wiped with PBS solution containing 10 μg/ml ClyO, after 10 s-2 min, the skin was wiped with 75% ethanol again. The tampon was put in the liquid medium for *Staphylococcus* culture after repeating several times, after being cultured overnight, the bacterial culture was diluted for plate counting. For the negative control group, the skin was only wiped with 75% ethanol. The tampon was put in the liquid medium for *Staphylococcus* culture after repeating several times. After being cultured overnight, the bacterial culture was diluted for plate counting. The resulting statistical graph was shown in FIG. 11. The result showed that ClyO was able to effectively eliminate *S. epidermidis* on surface of skin.

The invention claimed is:

1. A recombinant *Staphylococcus* lysin protein, wherein the amino acid sequence of said lysin is shown in SEQ. ID.NO.2.

2. A gene encoding the recombinant *Staphylococcus* lysin protein according to claim 1, wherein the DNA sequence of said gene is shown in SEQ.ID.NO.1.

3. A method of soluble expression and purification of the recombinant *Staphylococcus* lysin protein according to claim 1, wherein the gene according to claim 2 is cloned and then ligated with the expression vector pBAD24 to form an expression plasmid, the expression plasmid is transferred into *E. coli* strain BL21(DE3);

expression of the expression plasmid is induced in the *E. coli* strain BL21(DE3) by using 0.2% L-arabinose, the *E. coli* strain BL21(DE3) are collected and sonicated, forming a supernatant the supernatant is precipitated using 33% ammonium sulfate to form a precipitate, the precipitate is dissolved in PBS and then dialyzed against PBS overnight to form a crude extract solution, the crude extract solution after dialysis or the supernatant after sonication is passed through a HiTrap Q Sepharose FF column to collect an effluent, the effluent is then passed through a HiTrap SP Sepharose FF column to obtain a sample, the sample is gradient-eluted by 1M NaCl and elution peaks are collected in fractions, and the fractions with activity are combined and dialyzed against PBS overnight to obtain a sample of the purified lysin protein.

4. A method for killing *Staphylococcus epidermidis, Staphylococcus saprophyticus, Staphylococcus equorum, Staphylococcus capitis, Staphylococcus albus, Staphylococcus xylosus, Staphylococcus sciuri, Staphylococcus haemolyticus, Staphylococcus chromogens*, or *Staphylococcus aureus* in vitro comprising the use of the mixing an effective amount of recombinant *Staphylococcus* lysin protein according to claim 1 with a *Staphylococcus* bacteria suspension.

5. The method according to claim 4, wherein the *Staphylococcus aureus* include methicillin-sensitive *Staphylococcus aureus* and methicillin-resistant *Staphylococcus aureus*.

6. A pharmaceutical product comprising the recombinant *Staphylococcus* lysin protein of claim 1 as an active ingredient.

7. A method for detection and characterization of *Staphylococcus* via ATP or DNA released from the *Staphylococcus* wherein the method comprises:

mixing a *Staphylococcus* sample with the recombinant *Staphylococcus* lysin protein according to claim 1 to form a *Staphylococcus* mixture;

adding luciferase and its substrate to the *Staphylococcus* mixture, incubating the mixture at 37° C., and detecting a change of fluorescence intensity of the *Staphylococcus* mixture using a microplate reader, wherein a *Staphylococcus* sample without the recombinant *Staphylococcus* lysin protein according to claim 1 is a negative control.

8. A method for detection and characterization of *Staphylococcus*, wherein the method comprises:

mixing a *Staphylococcus* sample with the recombinant *Staphylococcus* lysin protein according to claim 1 to form a *Staphylococcus* mixture;

incubating the mixture at 37° C. for 10-15 min, centrifuging the mixture at 10,000 g for 1 min to form a pellet and supernatant, collecting the supernatant as a template, contacting the supernatant with two pairs of primers to determine if the *Staphylococcus* sample is a Methicillin-resistant *Staphylococcus aureus* strain, wherein the first pair of primers is FemB-F (SEQ.ID.NO.5) and FemB-R (SEQ.ID.NO.6) to amplify femB gene; the second pair of primers is MecA-F (SEQ.ID.NO.7) and MecA-R (SEQ.ID.NO.8) to amplify mecA gene;

amplifying by PCR the femB gene and the mecA gene, wherein the amplifying comprises incubating the supernatant and two pairs of primers 1) at 94° C. for 5 minutes; 2) performing 30 cycles of 94° C. for 30 seconds, 50° C. for 45 seconds, 72° C. for 60 seconds, and 3) 72° C. for 10 minutes to form a PCR product, and analyzing the PCR product by electrophoresis to identify whether a strain is Methicillin-resistant *Staphylococcus aureus* or not.

9. The method according to claim 8, for confirmed Methicillin resistant *Staphylococcus aureus* strain, further comprising:

contacting the supernatant with 4 pairs of primers, wherein the pairs of primers is β (SEQ.ID.NO.9) and α3 (SEQ.ID.NO.10) to amplify the ccrA2-B gene; ccrCF (SEQ.ID.NO.11) and ccrCR (SEQ.ID.NO.12) to amplify the ccrC gene; 1272F1 (SEQ.ID.NO.13) and 1272R1 (SEQ.ID.NO.14) to amplify the IS1272 gene; and 5RmecA (SEQ.ID.NO.15) and 5R413 (SEQ.ID.NO.16) to amplify the mecA-IS431 gene;

amplifying by PCR the ccrA2-B gene, the ccrC gene, the IS1272 gene and the mecA-IS431 gene to form a PCR product, and analyzing the PCR product by electrophoresis for Staphylococcal Cassette Chromosome Mec typing of the Methicillin resistant *Staphylococcus aureus* strain.

\* \* \* \* \*

SEQUENCE LISTING

<160> NUMBER OF SEQ ID NOS: 16

<210> SEQ ID NO 1
<211> LENGTH: 777
<212> TYPE: DNA
<213> ORGANISM: Artificial Sequence
<220> FEATURE:
<223> OTHER INFORMATION: synthetic construct

<400> SEQUENCE: 1

```
atggcactgc ctaaaacggg taaaccaacg gcaaaacagg tggttgactg ggcaatcaat      60
ttaatcggca gtggtgtcga tgttgatggt tattatggtc ggcaatgttg ggatttacct     120
aactatattt ttaatagata ctggaacttt aagacaccag gcaacgcaag agatatggca     180
tggtatagat atcctgaagg gtttaaagtg tttagaaaca cttctgattt tgtccctaaa     240
ccaggtgata tagcagtgtg gacaggtggt aattacaatt ggaacacttg gggacacact     300
ggtattgttg taggtccatc aactaaaagt tacttttata gtgtagatca gaattggaat     360
aactctaact cttacgttgg tagtcctgca gcaaagataa aacatagtta ttttggtgta     420
actcattttg ttagacccgc atacaaagca gaaccgaaac ctacaccacc aggtaccccg     480
cctggcacgg tcgcacagtc agcaccgaac cttgcaggct ctcgttccta tcgcgagacg     540
ggcactatga ctgtcacggt cgatgctctc aatgttcgcc gcgcgccaaa tacttcaggc     600
gagattgtag cagtatacaa gcgtggtgaa tcatttgact atgatactgt catcatcgat     660
gtcaatggct atgtctgggt gtcttacatt ggcggcagcg gcaaacgtaa ctacgttgcg     720
acgggcgcta ccaaagacgg taagcgtttc ggcaatgctt ggggtacatt taaataa      777
```

<210> SEQ ID NO 2
<211> LENGTH: 258
<212> TYPE: PRT
<213> ORGANISM: Artificial Sequence
<220> FEATURE:
<223> OTHER INFORMATION: Synthetic Construct

<400> SEQUENCE: 2

```
Met Ala Leu Pro Lys Thr Gly Lys Pro Thr Ala Lys Gln Val Val Asp
1               5                   10                  15

Trp Ala Ile Asn Leu Ile Gly Ser Val Asp Val Asp Gly Tyr Tyr
            20                  25                  30

Gly Arg Gln Cys Trp Asp Leu Pro Asn Tyr Ile Phe Asn Arg Tyr Trp
        35                  40                  45

Asn Phe Lys Thr Pro Gly Asn Ala Arg Asp Met Ala Trp Tyr Arg Tyr
    50                  55                  60

Pro Glu Gly Phe Lys Val Phe Arg Asn Thr Ser Asp Phe Val Pro Lys
65              70                  75                  80

Pro Gly Asp Ile Ala Val Trp Thr Gly Gly Asn Tyr Asn Trp Asn Thr
                85                  90                  95

Trp Gly His Thr Gly Ile Val Val Gly Pro Ser Thr Lys Ser Tyr Phe
            100                 105                 110

Tyr Ser Val Asp Gln Asn Trp Asn Asn Ser Asn Ser Tyr Val Gly Ser
        115                 120                 125

Pro Ala Ala Lys Ile Lys His Ser Tyr Phe Gly Val Thr His Phe Val
    130                 135                 140

Arg Pro Ala Tyr Lys Ala Glu Pro Lys Pro Thr Pro Pro Gly Thr Pro
145                 150                 155                 160

Pro Gly Thr Val Ala Gln Ser Ala Pro Asn Leu Ala Gly Ser Arg Ser
                165                 170                 175

Tyr Arg Glu Thr Gly Thr Met Thr Val Thr Val Asp Ala Leu Asn Val
            180                 185                 190

Arg Arg Ala Pro Asn Thr Ser Gly Glu Ile Val Ala Val Tyr Lys Arg
        195                 200                 205

Gly Glu Ser Phe Asp Tyr Asp Thr Val Ile Ile Asp Val Asn Gly Tyr
    210                 215                 220

Val Trp Val Ser Tyr Ile Gly Gly Ser Gly Lys Arg Asn Tyr Val Ala
225                 230                 235                 240

Thr Gly Ala Thr Lys Asp Gly Lys Arg Phe Gly Asn Ala Trp Gly Thr
                245                 250                 255

Phe Lys
```

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
ttaaccatgg gcatggcact gcctaaaacg                30

<210> SEQ ID NO 4
<211> LENGTH: 28
<212> TYPE: DNA
<213> ORGANISM: Artificial Sequence
<220> FEATURE:
<223> OTHER INFORMATION: Synthetic Construct

<400> SEQUENCE: 4
atatctcgag tttaaatgta ccccaagc                                28

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ttacagagtt aactgttacc                                         20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
atacaaatcc agcacgctct                                         20

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct

<400> SEQUENCE: 7
gtagaaatga ctgaacgtcc gataa                                   25

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
ccaattccac attgtttcgg tctaa                                   25

<210> SEQ ID NO 9
<211> LENGTH: 22
<212> TYPE: DNA
<213> ORGANISM: Artificial Sequence
<220> FEATURE:
<223> OTHER INFORMATION: Synthetic Construct

<400> SEQUENCE: 9
attgccttga taatagccyt ct                                      22

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
taaaggcatc aatgcacaaa cact                                    24

```
<210> SEQ ID NO 11
<211> LENGTH: 27
<212> TYPE: DNA
<213> ORGANISM: Artificial Sequence
<220> FEATURE:
<223> OTHER INFORMATION: Synthetic Construct

<400> SEQUENCE: 11
cgtctattac aagatgttaa ggataat                                          27

<210> SEQ ID NO 12
<211> LENGTH: 28
<212> TYPE: DNA
<213> ORGANISM: Artificial Sequence
<220> FEATURE:
<223> OTHER INFORMATION: Synthetic Construct

<400> SEQUENCE: 12
cctttataga ctggattatt caaaatat                                         28

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
gccactcata acatatggaa                                                  20

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
catccgagtg aaacccaaa                                                   19

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
tataccaaac ccgacaacta c                                                21

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
cggctacagt gataacatcc                                                  20
```